(12) United States Patent
Perullo

(10) Patent No.: US 8,905,978 B2
(45) Date of Patent: Dec. 9, 2014

(54) NON-REOPENING TUBING CLAMP AND METHOD OF USE THEREOF

(71) Applicant: Haemonetics Corporation, Braintree, MA (US)

(72) Inventor: John F. Perullo, Rowley, MA (US)

(73) Assignee: Haemonetics Corporation, Braintree, MA (US)

( * ) Notice: Subject to any disclaimer, the term of this patent is extended or adjusted under 35 U.S.C. 154(b) by 0 days.

(21) Appl. No.: 13/804,699

(22) Filed: Mar. 14, 2013

(65) Prior Publication Data

US 2014/0259548 A1    Sep. 18, 2014

(51) Int. Cl.
*A61M 5/00*    (2006.01)
*F16L 21/00*    (2006.01)

(52) U.S. Cl.
CPC .................................. *F16L 21/007* (2013.01)
USPC .............................................. 604/250; 251/4

(58) Field of Classification Search
CPC .............. A61M 39/28; A61M 39/284; A61M 2039/28; F16K 7/063
USPC ..................... 604/250; 251/9, 10, 4
See application file for complete search history.

(56) References Cited

U.S. PATENT DOCUMENTS

| 4,453,295 | A  | * | 6/1984  | Laszczower .................... 251/10 |
| 5,203,056 | A  | * | 4/1993  | Funk et al. ...................... 24/543 |
| 6,089,527 | A  | * | 7/2000  | Utterberg .......................... 251/4 |
| 6,644,618 | B1 | * | 11/2003 | Balbo ............................. 251/10 |
| 8,517,970 | B2 | * | 8/2013  | Mathias et al. .............. 604/6.15 |

FOREIGN PATENT DOCUMENTS

WO    WO 2007112500 A1 * 10/2007

* cited by examiner

*Primary Examiner* — Theodore Stigell
(74) *Attorney, Agent, or Firm* — Sunstein Kann Murphy & Timbers LLP

(57) ABSTRACT

A medical tubing clamp includes a first member, a second member, and a hinge connecting the first and second members to form a body. The second member has a first and second wall portion extending distally toward the first member, and a shelf extending between and connecting the first and second wall portions. The first and second wall portions and the shelf define a recess. The hinge allows the first and second members to move relative to one another to transition the clamp between an open mode and a closed mode. The first member is located within the recess and supported by the shelf when in the closed mode. The hinge has a first opening configured to receive the tubing. The clamp also has a tubing closure member that deforms the tubing to prevent fluid flow through the tubing when in the closed mode.

32 Claims, 4 Drawing Sheets

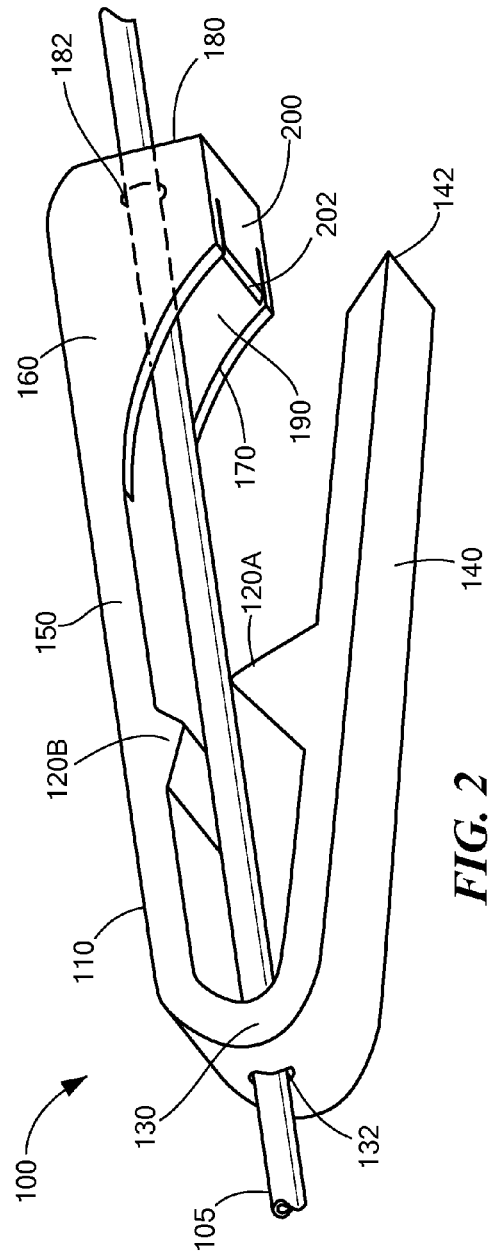
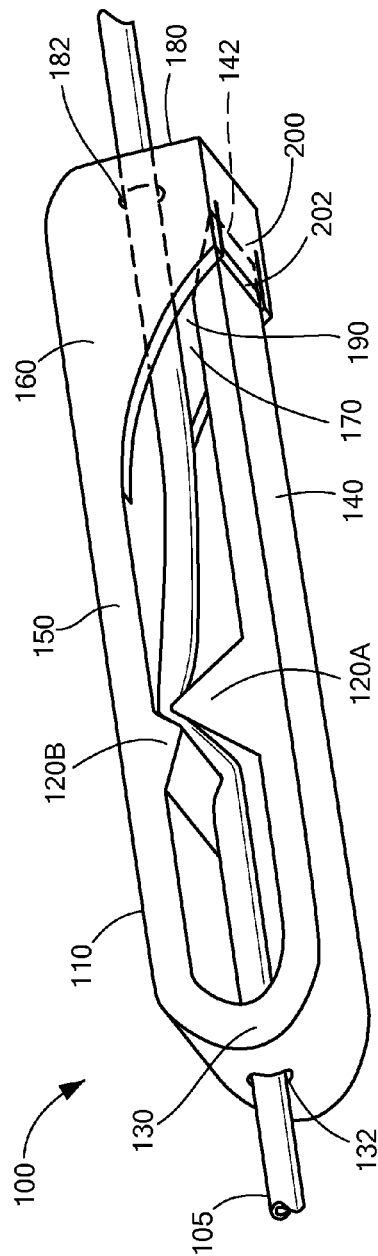
FIG. 2
FIG. 3

NON-REOPENING TUBING CLAMP AND METHOD OF USE THEREOF

TECHNICAL FIELD

The present invention relates to tubing clamps, and more particularly to non-reopening tubing clamps that prevent accidental opening of the clamp.

BACKGROUND ART

Disposable tubing sets are used in a number of blood collection and blood processing procedures. These tubing sets typically include a variety of collection containers that are connected to one another (and any blood processing equipment) by lengths of flexible tubing. Additionally, some sets also include a venous access device (e.g., a needle) that may be inserted into the patient's arm. At various points during the blood collection and processing one or more of the lengths of tubing may need to be closed off to prevent fluid flow through that section of tubing. To accomplish this, the tubing sets may include clamps located at various points on the tubing. These clamps, when closed, deform the tubing so that fluid is unable to flow past the clamp.

In some instances, it may be necessary to permanently or semi-permanently close off the fluid path through a tube. However, due to the flexible material used to manufacture them, many prior art clamps can be accidentally and/or erroneously opened by simply deforming a portion of the clamp. This, in turn, can negatively impact the collection/processing procedure.

SUMMARY OF THE EMBODIMENTS

In a first embodiment of the invention there is provided a medical tubing clamp having a first member, a second member, and a hinge connecting the first and second members to form a body. The second member may have a first and second wall portion that extend distally toward the first member, and a shelf that extends between the first and second wall portions. The first and second wall portions and the shelf may define a recess. The hinge may allow the first and second members to move relative to one another to transition the clamp between an open mode and a closed mode. The first member may be located within the recess and may be supported by the shelf when in the closed mode. The hinge has a first opening for receiving the tubing. The clamp may also have a tubing closure member (on the first or second member) that deforms the tubing to prevent fluid flow through the tubing when in the closed mode.

In some embodiments, the second member may include a third wall portion that extends distally toward the first member. The third wall portion may connect the first and second wall portions, and have a second opening configured to receive the tubing. The first, second, and third wall portions may resist deformation along a longitudinal axis of the clamp to prevent the clamp from returning toward the open mode. The clamp may also have a second tubing closure member that deforms the tubing to prevent fluid flow through the tubing when in the closed mode. The first tubing closure member may be located on the first member, and the second tubing closure member may be located on the second member.

In some embodiments, an end of the first member may include a first angled surface, and an end of the shelf may include a second angled surface. The first and second angled surfaces may slide along one another to allow the second member to enter the recess. Additionally, a portion of the first member may be narrower than a width of the recess, and the first and second wall portions may be configured to prevent lateral movement of the first member within the recess. The clamp may also include a thumb pad extending from at least one of the first and second members. The first member, the second member, and the hinge may define a hollow interior through which the tubing may pass.

In accordance with additional embodiments, a method of controlling fluid flow through a tubing may include providing a tubing clamp having a first member, a second member, and a hinge. The second member may have a first and second wall portion extending distally toward the first member, and a shelf extending between the first and second wall portions. The first and second wall portions, and the shelf may define a recess. The hinge may connect the first and second members to form a body, and may allow the first and second member to move relative to one another to transition the clamp from an open mode to a closed mode. The hinge may also have a first opening configured to receive the tubing. The clamp may also include a tubing closure member that deforms the tubing to prevent fluid flow through the tubing when in the closed position.

The method may also include (1) applying a force to the body to move the first member and second member relative to one another about the hinge, and (2) locking the tubing clamp in the closed position by pushing the first member past the shelf such that the first member is located within the recess and supported by the shelf. As the first and second members move, the tubing closure compresses the tubing. In some embodiments, the method may include placing the tubing clamp over the tubing such that the tubing extends through the hinge opening and along a longitudinal axis of the clamp.

In accordance with further embodiments, the second member may include a third wall portion extending distally toward the first member. The third wall portion may connect the first and second wall portions, and have a second opening configured to receive the tubing. The first, second, and third wall portions may resist deformation along a longitudinal axis of the clamp to prevent the clamp from returning toward the open mode. The tubing clamp may also include a second tubing closure member that compresses the tubing as the first member and second member move towards one another. The first tubing closure member may be located on the first member, and the second tubing closure member may be located on the second member.

In some embodiments, an end of the first member may include a first angled surface and an end of the shelf may include a second angled surface. In such embodiments, locking the tubing clamp in the closed mode may include causing the first angled surface to slide along the second angled surface such that the first member enters the recess. At least a portion of the first member may be narrower than a width of the recess, and the first and second wall portions may be configured to prevent lateral movement of the first member within the recess.

In accordance with further embodiments, a medical tubing clamp includes a first member, a second member, and a hinge. The second member may have a first portion and a reinforced portion extending from the first portion to an end wall, and toward the first member. The end wall may extend below the reinforced portion and may include a shelf extending from a distal end of the end wall. The reinforced portion may have an opening for receiving the tubing. The hinge may connect the first and second members to form a body, and may allow the first and second members to move relative to one another to transition the clamp between an open mode and a closed mode. The first member may be supported by the shelf when in the closed mode. The hinge may include a second opening configured to receive the tubing. The clamp may also include a tubing closure member that deforms the tubing to prevent fluid flow through the tubing when in the closed mode.

In some embodiments, the clamp may also include a channel located between a bottom surface of the reinforced portion and the shelf. A portion of the first member may be located within the channel when in the closed mode. The reinforced portion may strengthen the end wall to resist deformation along a longitudinal axis of the clamp. The tubing member may be located on the first or second member. The clamp may also include a second tubing closure member that deforms the tubing to prevent fluid flow through the tubing when in the closed position. In such embodiments, the first tubing member may be located on the first member, and the second tubing member may be located on the second member.

An end of the first member may include a first angled surface, and an end of the shelf may include a second angled surface. The first and second angled surfaces may slide along one another allow the first member slide past the shelf. The first member, second member, and the hinge may define a hollow interior through which the tubing may pass. The shelf may include an angled upper surface that presses at least a portion of the first member against a bottom surface of the reinforced portion when in the closed mode.

BRIEF DESCRIPTION OF THE DRAWINGS

The foregoing features of embodiments will be more readily understood by reference to the following detailed description, taken with reference to the accompanying drawings, in which:

FIG. 2 schematically shows a side view of a tubing clamp on medical tubing and in an open mode, in accordance with various embodiments of the present invention.

FIG. 3 schematically shows a side view of the tubing clamp shown in FIG. 2 on medical tubing and in a closed mode, in accordance with various embodiments of the present invention.

DETAILED DESCRIPTION OF SPECIFIC EMBODIMENTS

Figure 1:
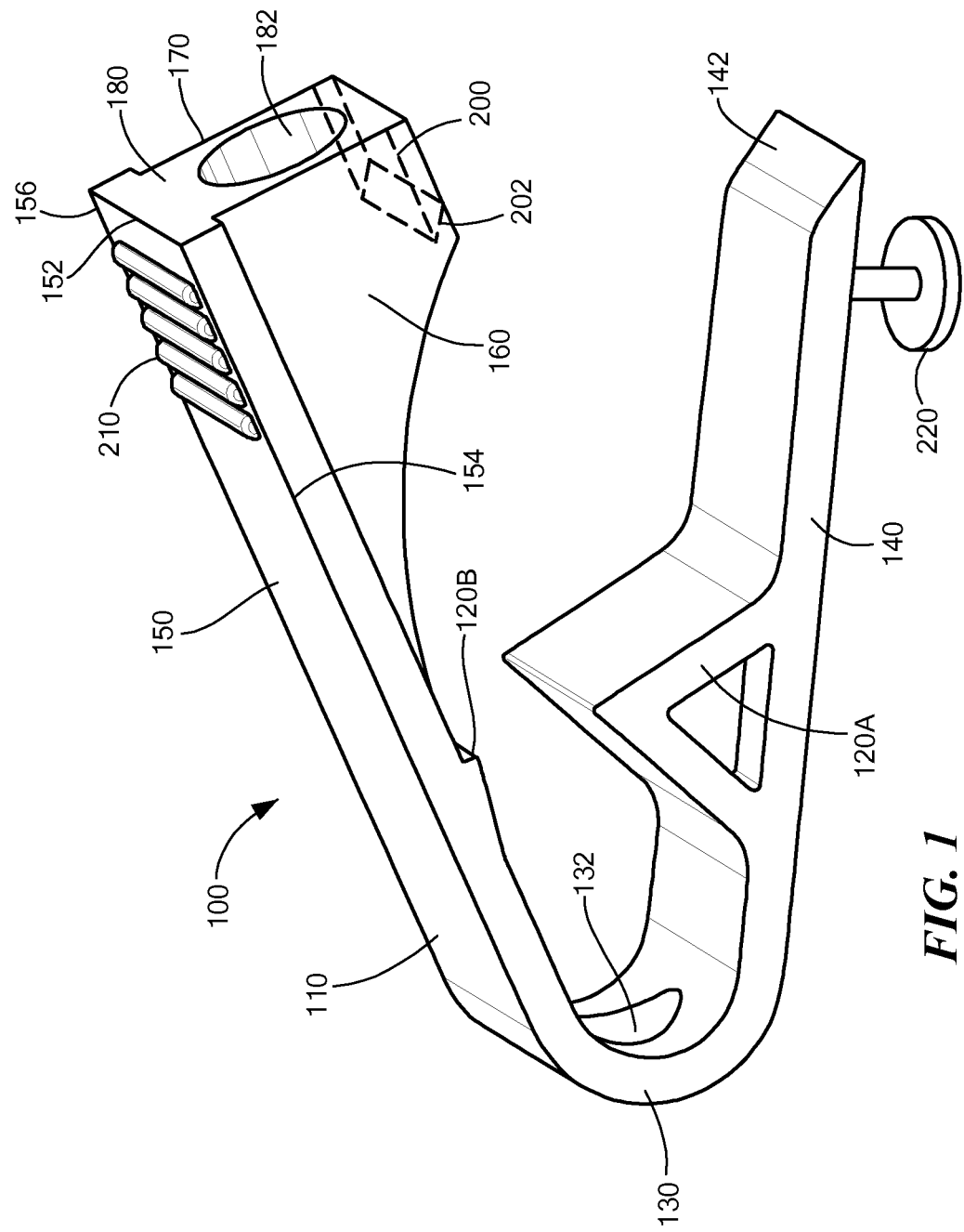
FIG. 1 is a perspective view of a first embodiment of a non-reopening tubing clamp in accordance with an embodiment of the present invention.

FIG. 1 shows a perspective view of a non-reopening tubing clamp in accordance with various embodiments of the present invention. FIGS. 2 and 3 show a clamp that operates in the same manner as the FIG. 1 clamp, but has a somewhat different design. As discussed in greater detail below, the tubing clamp 100 may have various features that help prevent the accidental re-opening of the tubing clamp 100. As shown in FIG. 1, the tubing clamp 100 has a body 110 that defines the structure of the device and tubing closure members 120A/B that deform the tubing when the clamp 100 is in the closed mode (see below discussion of FIG. 3). Additionally, the body 110 may include a hinge 130 that allows the clamp 100 to flex. In some embodiments, the hinge 130 can be a living hinge that is integrally formed within the body 110. The hinge 130 connects a first member 140 (e.g., a first/lower arm) and a second member 150 (e.g., a second/upper arm), and allows the first and second members 140/150 to flex towards one another in order to transition the clamp 100 from the open mode (shown in FIGS. 1 and 2) to the closed mode (shown in FIG. 3).

Near an end 152 of the second member 150, the second member 150 can have a number of walls extending towards (e.g., distally) the first member 140. For example, the second member 150 may have a first wall 160 (e.g., a front wall) extending distally from a front edge 154 of the second member 150, and a second wall 170 (e.g., a back wall) extending distally from a back edge 156 of the second member 150. Additionally, in some embodiments, the clamp 100 can also include an end wall 180 that connects the first and second walls 160/170 and extends distally from the end 152 of the second member 150. As discussed in greater detail below, the first wall 160, second wall 170, and the end wall 180 define a recess 190 in which the first member 140 resides when the clamp 100 is in the closed mode.

In order to lock the first member 140 in place within the recess 190 when the clamp 100 is in the closed mode, the clamp 100 can also include a shelf 200 located between (and connecting) the lower ends of the first wall 160, second wall 170, and end wall 180. When the clamp 100 is in the closed mode, the shelf 200 supports the first member 140 within the recess 190 and prevents first member 140 from returning towards the open mode (e.g., its at-rest position). To more easily allow the first member 140 to move past the shelf 200, both the shelf 200 and the first member 140 can have an angled surface. For example, the first member 140 can have a lower ramped surface 142 (e.g., towards the end of the first member 140), and the shelf 200 can have an upper ramped surface 202. As discussed in greater detail below, the upper and lower ramped surfaces 202/142 can slide along one another (e.g., to allow the first member 140 to more easily pass the shelf 200) as the clamp 100 is closed and the first member 140 is locked in place.

As mentioned above, some embodiments of the clamp 100 can have one or more tubing closure members that deform the tubing when the clamp 100 is closed. As shown in FIG. 1, one tubing closure member 120A may be larger than the other closure member 120B. Additionally, the closure members 120A/120B may not be aligned with one another (e.g., they may be located at different locations along the longitudinal axis of the clamp 100). In this manner, the closure members 120A/120B will contact the tubing at different locations along the length of the tubing.

It is important to note, that although FIGS. 1 through 3 show two closure members (e.g., a smaller closure member 120B located on the second member 150 and a larger closure member 120A located on the first member 140), other embodiments can have a different number of closure members and/or a different configuration. For example, some embodiments may only have a single large closure member located on either the first member 140 or second member 150. Alternatively, the tubing closures 120A/B on the first and second members 140/150 may be the same size and/or aligned with one another (e.g., such that the points/ends of the closure members 120A/B contact the tubing 105 at the same point along the length of the tubing 105). In still further embodiments, the clamp 100 may have two tubing closure members located on one of the arms/members (e.g., either the first or second member 140/150) and one closure member located on the other. In such embodiments, the single closure member may be located between the closure members located on the opposing arm/member.

To accommodate the tubing 105, the hinge 130 can have a hinge opening 132 through which the tubing 105 can extend when the clamp 100 is placed on the tubing 105. Similarly, if the clamp 100 has an end wall 180, the end wall 180 can have an end wall opening 182 through which the tubing 105 can extend. Therefore, as shown in FIG. 2, when the clamp 100 is placed on the tubing 105, the tubing 105 will pass through the hinge opening 132, extend through the interior of the clamp 100 (e.g., between the first and second member 140/150), and will pass through the end wall opening 182.

As mentioned above, to close the clamp 100, the first and second members 140/150 may be flexed towards one another (for example, by applying a force to the clamp 100) such that the first member 140 enters the recess 190 and is locked in place by the shelf 200. To help the user apply the required force and maintain a grip on the clamp 100, some embodiments may include a gripping surface 210 (e.g., a plurality of ribs) located on one side (e.g., on the second member 150) and a thumb pad 220 located on the other side (e.g., on the first member 140).

As mentioned above, various embodiments of the present invention prevent the accidental re-opening of the clamp 100 once it is closed. To that end, it is important to note that the first and second wall members 160/170 perform various functions that prevent the accidental re-opening. For example, because the first member 140 is located within the recess 190 defined, in part, by the first and second wall members 160/170, the first and second wall members 160/170 prevent the lateral movement of the first member 140 within the recess 190. Therefore, a user is not able to open the clamp 100 by laterally sliding the first member 140 out of the recess 190.

Additionally, the first and second walls 160/170 strengthen and increase the rigidity of the end wall 180. By increasing the strength and rigidity of the end wall 180, the first and second walls 160/170 prevent the end wall 180 from elastically deforming when a force is applied to the end wall 180. Therefore, because the end wall 180 is unable to deform (and the first and second walls 160/170 prevent lateral movement of the first member 140), the first member 140 remains trapped/locked within the recess 190, and the clamp 100 cannot be accidentally (or intentionally) re-opened.

In operation, to block the flow of fluid through the tubing 105, the user may first place the clamp 100 onto the tubing 105 by inserting the end of the tubing 105 into the hinge opening 132 (or the end wall opening 182), and threading the tubing 105 through the interior of the clamp 100 and out the end wall opening 182 (or the hinge opening 132). The user may then slide the clamp 100 along the tubing 105 until it is in the desired location on the tubing 105 (FIG. 2). Once in place on the tubing 105, the user may grasp the clamp 100 (e.g., on the gripping surface 210 and thumb pad 220, if equipped) and squeeze the clamp 100 (e.g., apply a force to the first and/or second member 140/150) to transition the clamp 100 from the open mode (FIG. 2) to the closed mode (FIG. 3). As the clamp 100 closed, the first and second members 140/150 will flex about the hinge 130 until the lower ramped surface 142 contacts the upper ramped surface 202. During this time, the tubing closure members 120A/120B will begin to deform the tubing 105 to prevent the flow of fluid through the tubing 104. As additional force is applied to the clamp 100, the lower ramped surface 142 will slide along the upper ramped surface 202 until the first member 140 snaps into the recess 190. Once in the recess 190, the first member 140 engages/is supported by (e.g., rests on) the top surface of the shelf 200. The clamp is now in the closed mode (FIG. 3.), and the tubing closure members 120A/120B have closed off the tubing 105.

Figure 4:
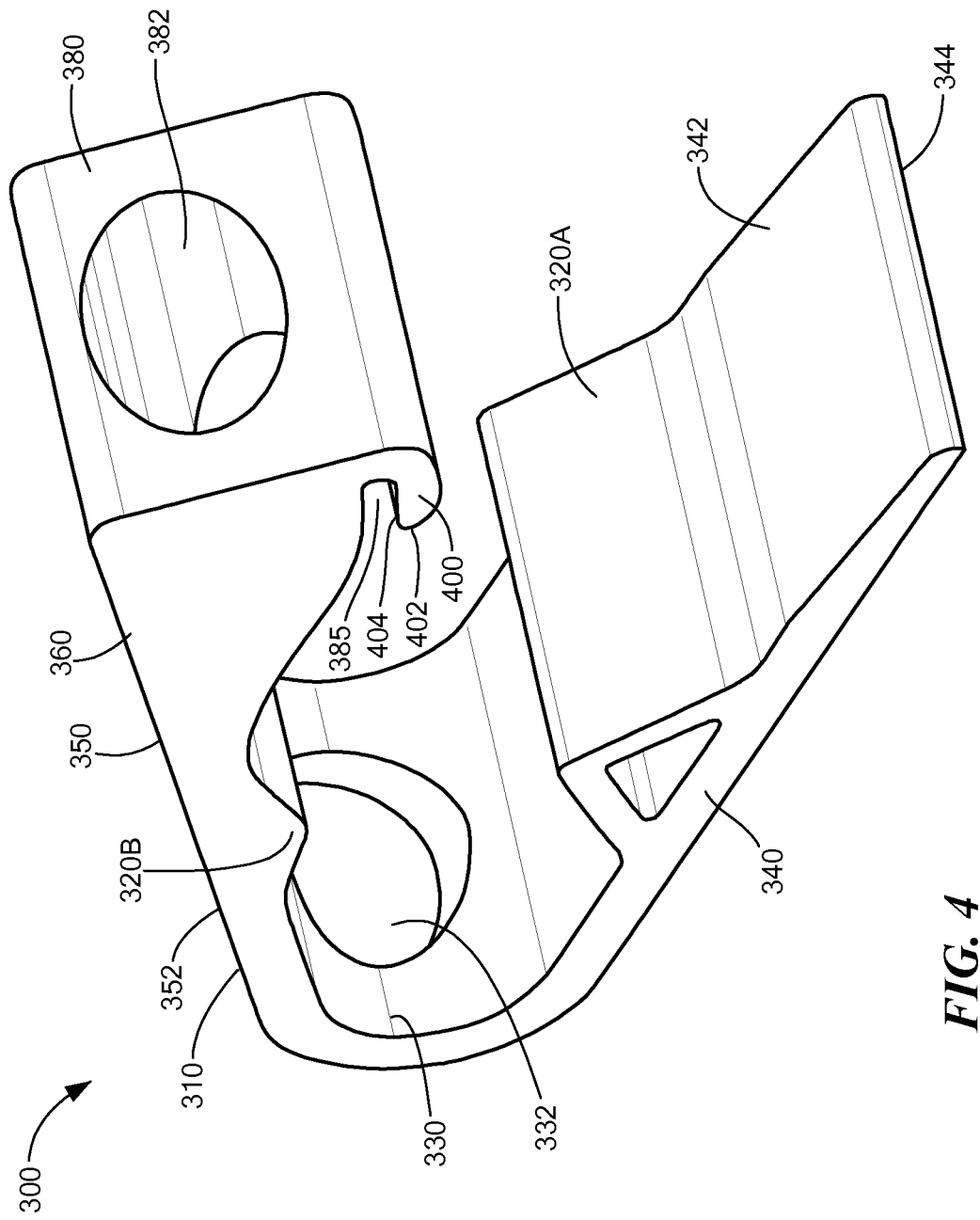
FIG. 4 is a perspective view of an alternative embodiment of a non-reopening tubing clamp in accordance with an embodiment of the present invention.
Figure 5:
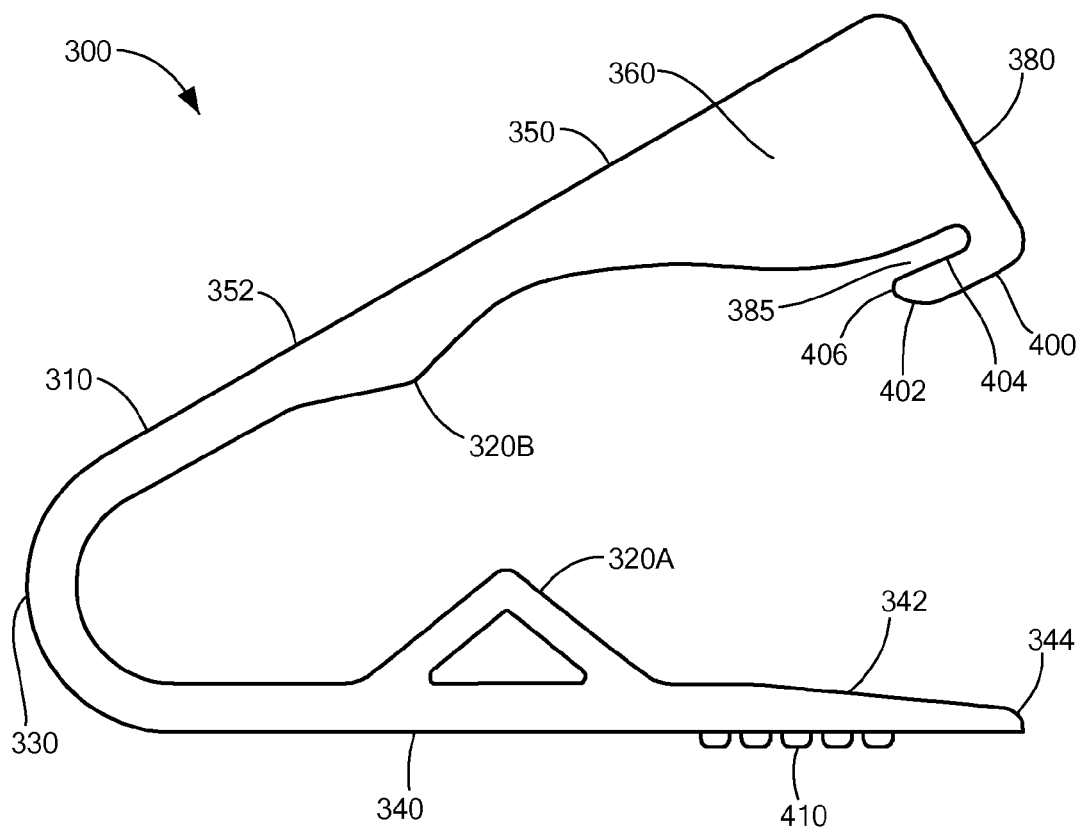
FIG. 5 schematically shows a side view of the tubing clamp shown in FIG. 4 on medical tubing and in an open mode, in accordance with various embodiments of the present invention.
Figure 6:
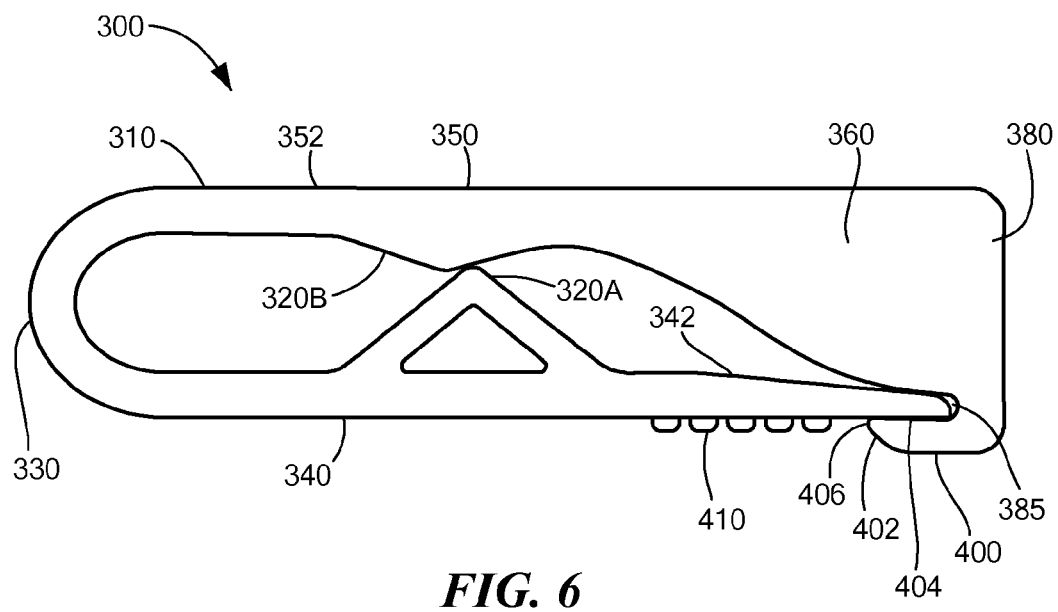
FIG. 6 schematically shows a side view of the tubing clamp shown in FIG. 5 on medical tubing and in a closed mode, in accordance with various embodiments of the present invention.

FIGS. 4 through 6 schematically show an alternative embodiment of a non-reopening clamp 300. Like the embodiments shown in FIGS. 1 through 3, the clamp 300 shown in FIGS. 4 through 6 has a body 310 that defines the structure of the clamp 300 and tubing closure members 320A/B that deform the tubing 105 when the clamp 300 is in the closed mode (FIG. 6). Additionally, the body 310 may include a hinge 330 that connects a first member 340 and a second member 350 and allows them to flex towards one another in order to transition the clamp 300 from the open mode (shown in FIGS. 4 and 5) to the closed mode (shown in FIG. 6).

Unlike the clamps 100 shown in FIGS. 1 through 3, the clamp 300 shown in FIGS. 4 through 6 does not have the first and second wall members 160/170 and the end wall 180 that extend from the second member. Instead, as best shown in FIG. 4, the second member 350 can have a reinforced portion 360 (e.g., a thickened portion) that extends from a point near the center of the clamp 300 (e.g., from the end of a thinner portion 352 of the second member 350) to the end wall 380. This reinforced portion 360 extends towards the first member 340 and performs a function similar to that of the first and second walls 160/170 discussed above. Specifically, the reinforced portion 360 provides some rigidity to the end wall 380 to prevent the end wall 380 from deforming when a force is applied to it. This, in turn, prevents the re-opening of the clamp 300.

To facilitate placing the clamp 300 over the tubing 105, the hinge 330 can have a hinge opening 332 passing through it. Similarly, the reinforced portion 360 can have a reinforced portion opening 382 passing through it. The hinge opening 332 and the reinforced portion opening 382 may be sized to receive the tubing 105. Additionally, to provide the tubing 105 with sufficient room within the interior of the clamp 300 (e.g., between the first and second members 340/350) and to avoid any interference with the tubing closure members 320A/320B, the reinforced portion 360 can be angled such that the thickness of the reinforced portion 360 increases towards the end wall 380.

Additionally, in some embodiments, the end wall 380 may extend down past the reinforced portion 360 to create a channel 385 between the bottom of the reinforced portion 360 and a shelf 400 that extends outward from the bottom of the end wall 380 (e.g., into the interior of the clamp 300). As shown in FIG. 6, when the clamp 300 is in the closed mode, the end of the first member 340 resides within the channel 385 and is supported by the shelf 400. In further embodiments, and as best shown in FIGS. 5 and 6, the upper surface 404 of the shelf 400 can be angled upwards (e.g., proximally; towards the second member 350) such that it presses the portion of the first member 340 within the channel against the bottom surface of the reinforced portion 360. In this manner, the shelf 400 is able to minimize lateral movement of the first member 340 within the channel 385 by creating a tight fit between the first member 340, the shelf 400, and the reinforced portion 360. This, in turn, improves the clamp's resistance to re-opening.

Operation of the clamp 300 is similar to that of the clamps shown in FIGS. 1 through 3. For example, after securing the clamp 300 to the tubing 105 (e.g., by passing the tubing 105 through the hinge opening 332 and reinforced portion opening 382), the user may grasp the clamp 300 (e.g., at the gripping portion 410) and squeeze the clamp 300 to cause the first and second members 340/350 to flex about the hinge 330 and move closer to one another. When the angled portion 342 of the first member 340 contacts the angled portion 402 of the shelf 400, the angled portion 342 of the first member 240 will slide along the angled portion 402 of the shelf 400 until the end of the first member 340 passes the shelf 400 and snaps into place within the channel 385. To further help the first member pass the shelf and enter the channel 385, the first member 340 and the shelf 400 can have rounded edges (e.g., first member rounded edge 344 and shelf rounded edge 406).

Once the first member 340 has engaged the shelf 400 and is located within the channel 385, the clamp 300 is in the closed mode. When in the closed mode the tubing closure members 320A/320B deform the tubing 105 to prevent fluid flow through the tubing Additionally, the upper surface 404 of the shelf 400 may press the first member 340 against the bottom surface of the reinforced portion to prevent/limit lateral movement.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A medical tubing clamp comprising:
   a first member;
   a second member having a first and second wall portion extending distally toward the first member, and a shelf extending between and connecting the first and second wall portions, the first and second wall portions and the shelf defining a recess;
   a hinge connecting the first and second members to form a body, the hinge configured to allow the first and second members to move relative to one another to transition the clamp between an open mode and a closed mode, the first member located within the recess and supported by and proximal to the shelf when in the closed mode, the hinge having a first opening configured to receive the tubing; and
   a tubing closure member configured to deform the tubing to prevent fluid flow through the tubing when in the closed mode.

2. A medical tubing clamp according to claim 1, wherein the second member includes a third wall portion extending distally toward the first member, the third wall portion connecting the first and second wall portions and having a second opening configured to receive the tubing, the shelf connecting the first, second and third wall portions.

3. A medical tubing clamp according to claim 2, wherein the first, second, and third wall portions are configured to resist deformation along a longitudinal axis of the clamp to prevent the clamp from returning toward the open mode.

4. A medical tubing clamp according to claim 1, wherein the tubing closure member is located on the first member.

5. A medical tubing clamp according to claim 1, wherein the tubing closure member is located on the second member.

6. A medical tubing clamp according to claim 1, further comprising:
   a second tubing closure member configured to deform the tubing to prevent fluid flow through the tubing when in the closed mode, the first tubing closure member being located on the first member, and the second tubing closure member being located on the second member.

7. A medical tubing clamp according to claim 1, wherein an end of the first member includes a first angled surface and an end of the shelf includes a second angled surface, the first and second angled surfaces configured to slide along one another as the clamp transitions towards the closed mode to allow the second member to enter the recess.

8. A medical tubing clamp according to claim 1, wherein at least a portion of the first member is narrower than a width of the recess.

9. A medical tubing clamp according to claim 1, wherein the first and second wall portions are configured to prevent lateral movement of the first member within the recess.

10. A medical tubing clamp according to claim 1, further comprising a thumb pad extending from at least one of the first and second members.

11. A medical tubing clamp according to claim 1, wherein the first member, second member, and the hinge define a hollow interior, the tubing passing through the hollow interior.

12. A method of controlling fluid flow through medical tubing comprising:
   providing a tubing clamp comprising:
      a first member;
      a second member having a first and second wall portion extending distally toward the first member, and a shelf extending between and connecting the first and second wall portions, the first and second wall portions and the shelf defining a recess,
      a hinge connecting the first and second members to form a body, the hinge configured to allow the first and second member to move relative to one another to transition the clamp from an open mode to a closed mode, the hinge having a first opening configured to receive the tubing, and
      a tubing closure member configured to deform the tubing to prevent fluid flow through the tubing when in the closed position;
   applying a force to the body to move the first member and second member relative to one another about the hinge, the tubing closure member compressing the tubing as the first member and second member move towards one another; and
   locking the tubing clamp in the closed mode by pushing the first member past the shelf such that the first member is located within the recess and supported by the shelf, the hinge biasing the first member toward the shelf when the clamp is in the closed mode.

13. A method according to claim 12, further comprising:
   placing the tubing clamp over the tubing such that the tubing extends through the hinge opening and along a longitudinal axis of the clamp.

14. A method according to claim 12, wherein the second member includes a third wall portion extending distally toward the first member, the third wall portion connecting the first and second wall portions and having a second opening configured to receive the tubing.

15. A method according to claim 14, wherein the first, second, and third wall portions are configured to resist deformation along a longitudinal axis of the clamp to prevent the clamp from returning toward the open mode.

16. A method according to claim 12, wherein the tubing closure member is located on the first member.

17. A method according to claim 12, wherein the tubing closure member is located on the second member.

18. A method according to claim 12, the tubing clamp further including a second tubing closure member, the second tubing closure member compressing the tubing as the first member and second member move towards one another, the first tubing member being located on the first member, and the second tubing member being located on the second member.

19. A method according to claim 12, wherein an end of the first member includes a first angled surface and an end of the shelf includes a second angled surface, locking the tubing clamp in the closed mode including causing the first angled surface to slide along the second angled surface such that the first member enters the recess.

20. A method according to claim 12, wherein at least a portion of the first member is narrower than a width of the recess.

21. A method according to claim 12, wherein the first and second wall portions are configured to prevent lateral movement of the first member within the recess.

22. A method according to claim 12, further comprising a thumb pad extending from at least one of the first and second members.

23. A medical tubing clamp comprising:
   a first member;
   a second member having a first portion and a reinforced portion extending from the first portion to an end wall, the reinforced portion also extending distally toward the first member, the end wall extending below the reinforced portion and including a shelf extending from a distal end of the end wall, the reinforced portion having an opening configured to receive the tubing;
   a hinge connecting the first and second members to form a body, the hinge configured to allow the first and second members to move relative to one another to transition the clamp between an open mode and a closed mode, the first member supported by the shelf when in the closed mode, the hinge having a second opening configured to receive the tubing; and
   a tubing closure member configured to deform the tubing to prevent fluid flow through the tubing when in the closed mode.

24. A medical tubing claim according to claim 23, further comprising a channel located between a bottom surface of the reinforced portion and the shelf, at least a portion of the first member located within the channel when in the closed mode.

25. A medical tubing clamp according to claim 23, wherein the reinforced portion is configured to strengthen the end wall to resist deformation along a longitudinal axis of the clamp.

26. A medical tubing clamp according to claim 23, wherein the tubing closure member is located on the first member.

27. A medical tubing clamp according to claim 23, wherein the tubing closure member is located on the first portion of the second member.

28. A medical tubing clamp according to claim 23, further comprising:
   a second tubing closure member configured to deform the tubing to prevent fluid flow through the tubing when in the closed position, the first tubing member being located on the first member, and the second tubing member being located on the second member.

29. A medical tubing clamp according to claim 23, wherein an end of the first member includes a first angled surface and an end of the shelf includes a second angled surface, the first and second angled surfaces configured to slide along one another as the clamp transitions toward the closed mode to allow the first member to slide past the shelf.

30. A medical tubing clamp according to claim 23, wherein the first member, second member, and the hinge define an interior, the tubing passing through the interior.

31. A medical tubing clamp according to claim 23, wherein the shelf includes an angled upper surface, the angled upper surface configured to press at least a portion of the first member against a bottom surface of the reinforced portion when in the closed mode.

32. A medical tubing clamp according to claim 23, wherein the opening in the reinforced portion extends through the end wall.

* * * * *